(12) United States Patent
Griffin

(10) Patent No.: US 7,935,140 B2
(45) Date of Patent: May 3, 2011

(54) DELIVERY DEVICE WITH ANCHORING FEATURES AND ASSOCIATED METHOD

(75) Inventor: Mark Alan Griffin, Louisville, KY (US)

(73) Assignee: Merit Medical Systems, Inc., South Jordan, UT (US)

( * ) Notice: Subject to any disclaimer, the term of this patent is extended or adjusted under 35 U.S.C. 154(b) by 1272 days.

(21) Appl. No.: 11/432,862

(22) Filed: May 12, 2006

(65) Prior Publication Data

US 2007/0100421 A1 May 3, 2007

Related U.S. Application Data

(60) Provisional application No. 60/680,678, filed on May 13, 2005.

(51) Int. Cl.
*A61F 2/06* (2006.01)

(52) U.S. Cl. .................. 623/1.11; 623/1.12; 623/1.23

(58) Field of Classification Search .............. 623/1.11, 623/1.12, 1.23, 903, 921
See application file for complete search history.

(56) References Cited

U.S. PATENT DOCUMENTS

| | | | | |
|---|---|---|---|---|
| 4,645,491 A | * | 2/1987 | Evans | 604/158 |
| 5,591,228 A | * | 1/1997 | Edoga | 128/898 |
| 5,702,418 A | | 12/1997 | Ravenscroft | |
| 5,707,376 A | | 1/1998 | Kavteladze et al. | |
| 5,843,166 A | * | 12/1998 | Lentz et al. | 623/1.13 |
| 5,876,448 A | | 3/1999 | Thompson et al. | |
| 5,893,867 A | | 4/1999 | Bagaoisan et al. | |
| 5,968,069 A | * | 10/1999 | Dusbabek et al. | 606/194 |
| 5,989,280 A | * | 11/1999 | Euteneuer et al. | 623/1.1 |
| 6,171,367 B1 | * | 1/2001 | Peng et al. | 95/46 |
| 6,607,551 B1 | * | 8/2003 | Sullivan et al. | 623/1.11 |
| 7,172,617 B2 | * | 2/2007 | Colgan et al. | 623/1.11 |
| 2002/0151955 A1 | * | 10/2002 | Tran et al. | 623/1.12 |
| 2004/0059404 A1 | | 3/2004 | Bjorklund et al. | |
| 2004/0176782 A1 | | 9/2004 | Hanse et al. | |
| 2006/0229697 A1 | * | 10/2006 | Gerdts et al. | 623/1.11 |

FOREIGN PATENT DOCUMENTS

| | | |
|---|---|---|
| EP | 1 208 816 A2 | 5/2002 |
| WO | WO 00/71058 A1 | 11/2000 |
| WO | WO 2006/105500 A1 | 10/2006 |
| WO | WO2006/124823 | 11/2006 |

OTHER PUBLICATIONS

International Search Report for PCT/US2006/018812, completed Mar. 16, 2007.
Written Opinion for PCT/US2006/018812, completed Mar. 16, 2007.
EP Communication for EP Application No. 06770397.5-1260 dated Jan. 22, 2009.

* cited by examiner

*Primary Examiner* — Eduardo C Robert
*Assistant Examiner* — Kevin Everage
(74) *Attorney, Agent, or Firm* — Stoel Rives LLP

(57) ABSTRACT

A delivery device for positioning and deploying an implantable device within a lumen is provided. The device includes an inner tube positioned within an outer tube and capable of sliding therein, wherein the inner and outer tubes have proximal and distal ends. A mechanism is coupled to at least one of the inner and outer tubes and is operable to deploy the implantable device within the lumen. At least one anchor is positioned on the inner tube to stabilize the implantable device by engaging at least a portion of the implantable device while the mechanism deploys the device. The anchor is positioned on the inner tube such that the anchor is freely rotatable about the inner tube.

36 Claims, 6 Drawing Sheets

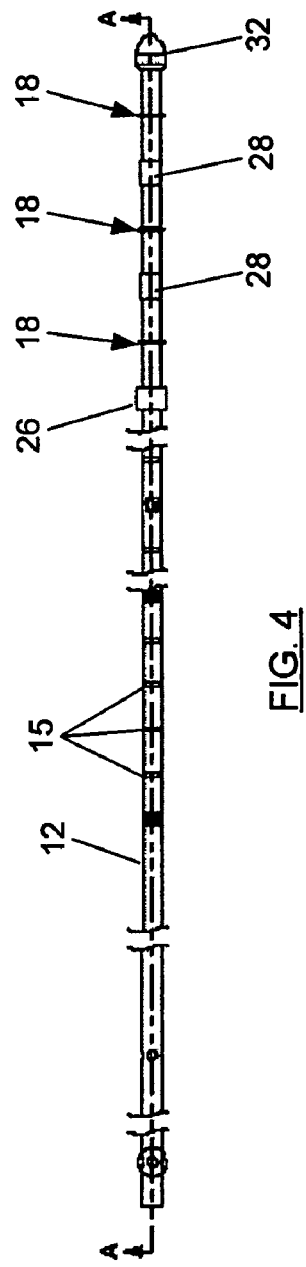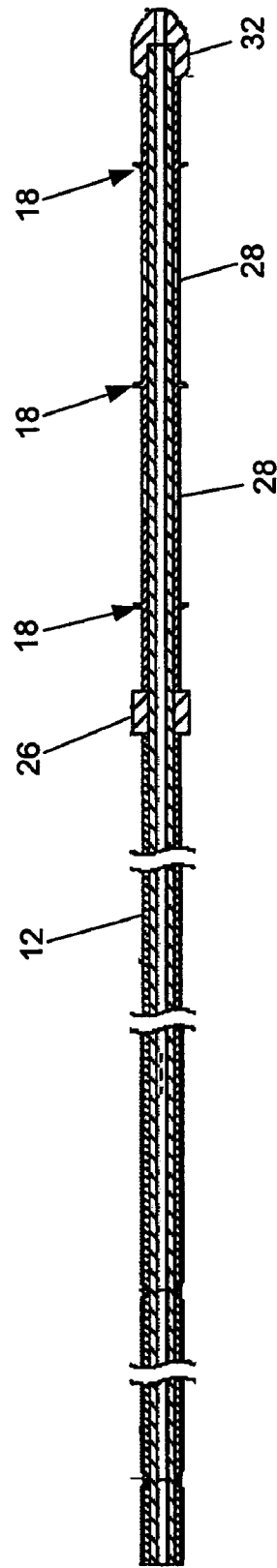
FIG. 4
FIG. 4A

DELIVERY DEVICE WITH ANCHORING FEATURES AND ASSOCIATED METHOD

CROSS-REFERENCE TO RELATED APPLICATIONS

The present application claims priority U.S. Provisional Application No. 60/680,678 entitled "Delivery Device with Anchoring Features and Associated Method," filed May 13, 2005, the contents of which are incorporated herein by reference.

BACKGROUND OF THE INVENTION

1) Field of the Invention

The present invention relates to a delivery device and, in more particular, to a delivery device that employs anchoring features to stabilize an implantable device during deployment of the implantable device within a lumen.

2) Description of Related Art

Stents are devices that are inserted into body lumina such as vessels or passages to keep the lumen open and prevent closure due to a stricture, external compression, or internal obstruction. In particular, stents are commonly used to keep blood vessels open in the coronary arteries, and they are frequently inserted into the ureters to maintain drainage from the kidneys, the bile duct for pancreatic cancer or cholangiocarcinoma, or the esophagus or airways for strictures or cancer. Vascular as well as nonvascular stenting has evolved significantly; unfortunately, there remain significant limitations with respect to effectively implanting the stents into a patient's lumen.

In order to serve its desired function, the stent should be delivered precisely and oriented correctly. Improper installation can lead to tissue luminal inflammation and tissue granulation. In order to facilitate the delivery of stents, devices, such as endoscopes and catheters, have been utilized to deploy stents more precisely. Unfortunately, guidance of the stent has substantially remained a function of physician skill resulting from substantial practice. This fact has become particularly evident with the advent of radially expanding stents. The physician frequently needs to measure the length of the lesion, align a distal end of the of the delivery device, and rely on accurate deployment to ensure that the entire lesion is covered by the stent. Moreover, when deploying the stent, a physician often displaces an outer tube relative to an inner tube, where the stent is positioned between the inner and outer tube. As the stent is deployed, the stent length often decreases due to friction between the outer tube and the stent. This decrease in stent length also decreases the positional accuracy of the deployed stent. In addition, increasing the stent column strength to compensate for length shortening affects the physical properties of the stent, which may in turn adversely affect the efficacy of the stent.

Techniques have been developed to address the problem of length foreshortening of the stent during deployment. For example, U.S. Pat. No. 6,607,551 to Sullivan et al. discloses a stent delivery system with a nested stabilizer. In particular, Sullivan discloses that the stabilizer, which is positioned within the interior of a stent, includes a surface element for engaging the stent in a region corresponding to a low-column-strength segment of the stent. The surface element could be one or more radial protuberances, as shown in FIG. 3A of Sullivan. The protuberances may include rings of various cross-sections, axial lengths, or spacing between the protuberances, or may be in the form of discrete barbs, bumps, or inflatable knobs arranged in a circumferential configuration or helical pattern about the stabilizer. The protuberances are attached to the stabilizer using techniques such as bonding or are formed in the stabilizer using techniques such as grinding.

The protuberances provide increased stabilization of the stent, especially for a low-column-strength segment, prior to deploying the stent. Despite these improvements, additional innovations in stabilizing and limiting foreshortening of an implantable device to promote more accurate delivery of the implantable device are desired.

Therefore, there is a need in the industry for a delivery device that is capable of effectively and accurately positioning an implantable device within a patient's lumen. In addition, there is a need for a delivery device that is capable of stabilizing the implantable device during deployment of the implantable device.

BRIEF SUMMARY OF THE INVENTION

The invention addresses the above needs and achieves other advantages by providing a delivery device for deploying an implantable device within a lumen. The delivery device includes anchors positioned on an inner tube for stabilizing the implantable device during deployment. The anchors provide a compressive force to the implantable device and an outer tube that reduces foreshortening of the device, which also reduces the potential for inaccurately positioning the device within the lumen.

In one embodiment of the present invention, a delivery device for positioning and deploying an implantable device within a lumen is provided. The device includes a longitudinal outer tube having proximal and distal ends, wherein the implantable device is positioned proximate to the distal end of the outer tube. The device also includes a longitudinal inner tube positioned within the outer tube and having proximal and distal ends, wherein the outer tube is capable of sliding over the inner tube. A mechanism is coupled to the inner and/or outer tubes and is operable to deploy the implantable device within the lumen. At least one anchor is positioned on the inner tube to stabilize the implantable device by engaging at least a portion of the implantable device while the mechanism deploys the device. The anchor is positioned on the inner tube such that the anchor is freely rotatable about the inner tube.

In various aspects of the delivery device, a coil is positioned within the outer tube. Each of the inner and outer tubes may include a semi-transparent polymeric material, such as polytetrafluoroethylene and/or polyether block amide. The mechanism could include at least one actuator coupled to the outer tube. A pusher may be positioned on the inner tube and adjacent to a proximal end of the implantable device. The anchor could be positioned adjacent to the pusher. Moreover, the outer tube could include a larger diameter sheath at its distal end that is positioned over and adjacent to the implantable device.

In additional aspects of the delivery device, there are a plurality of anchors. Each anchor includes an annular member that extends outward and radially about at least a portion of the circumference of the inner tube. Each annular member may extend outwardly and radially from a cylindrical member. In addition, each anchor is capable of applying a compressive force on at least a portion of the implantable device to frictionally engage the implantable device during deployment thereof. The delivery device may include at least one spacer positioned on the inner tube and adjacent to a respective anchor, wherein the spacer is also freely rotatable about the inner tube.

Furthermore, one aspect of the present invention provides a method for manufacturing a delivery device. The method includes forming a longitudinal inner tube having proximal and distal ends. The method also includes positioning at least one anchor on the inner tube such that the anchor is rotatable about the inner tube.

Variations of the method include forming an outer tube and/or positioning the outer tube over the inner tube such that the outer tube is capable of sliding over the inner tube. The method could also include attaching a sheath to a distal end of the outer tube. The method may include positioning a pusher on the inner tube and adjacent to the anchor. Moreover, the method could include positioning at least one spacer on the inner tube and adjacent to the anchor, wherein the spacer is freely rotatable about the inner tube. The method could include attaching a tip to the distal end to restrain the anchor and/or spacer on the inner tube. In one aspect of the present invention, the method further includes forming the anchor with injection molding prior to positioning the anchor on the inner tube.

BRIEF DESCRIPTION OF THE SEVERAL VIEWS OF THE DRAWINGS

Figure 1:
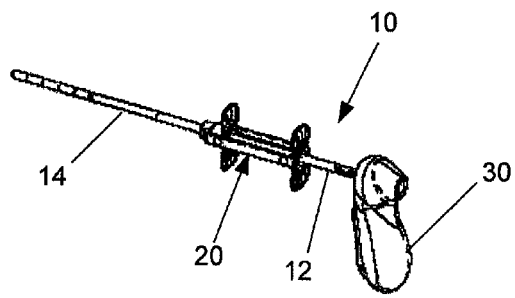
Figure 2:
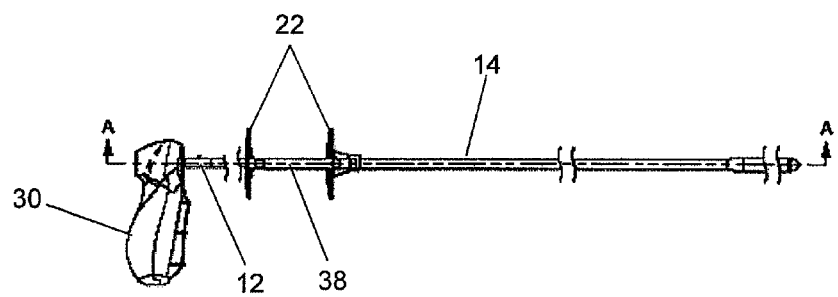
Figure 2A:
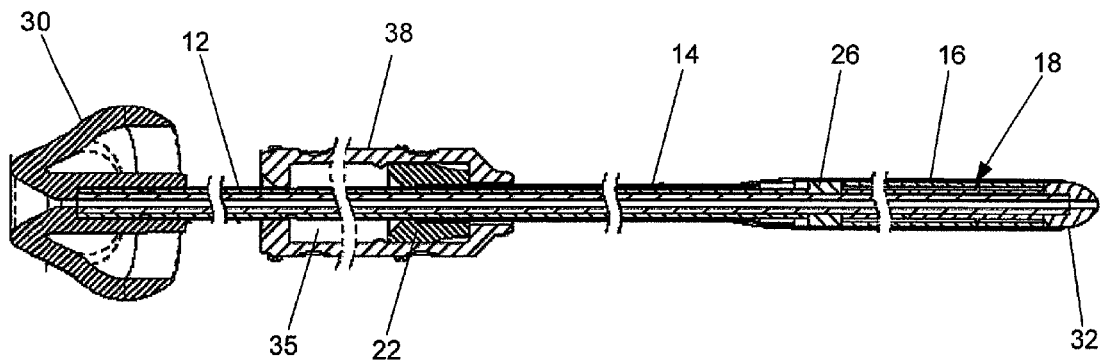
Figure 3:
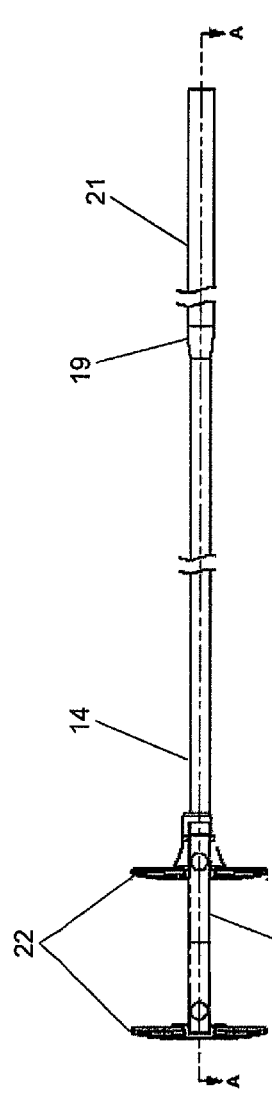
Figure 3A:
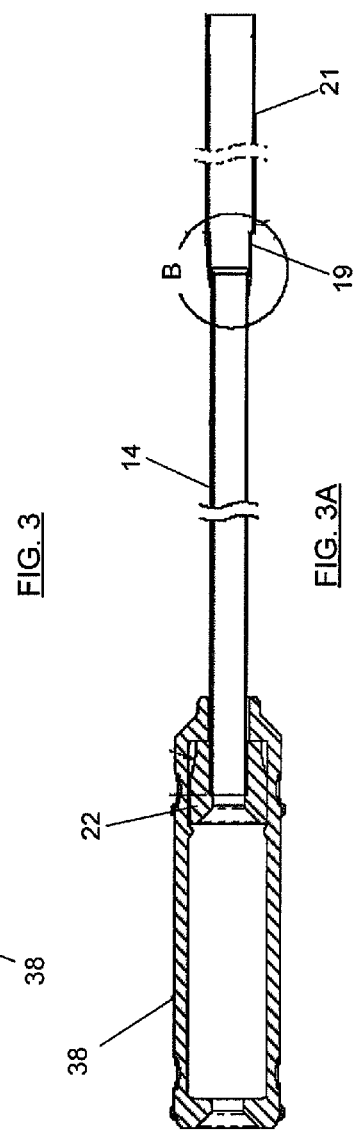
Figure 3B:
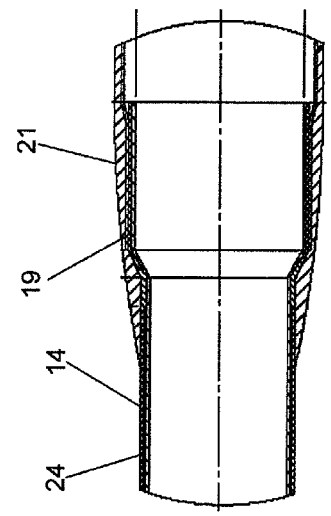
Figure 5:
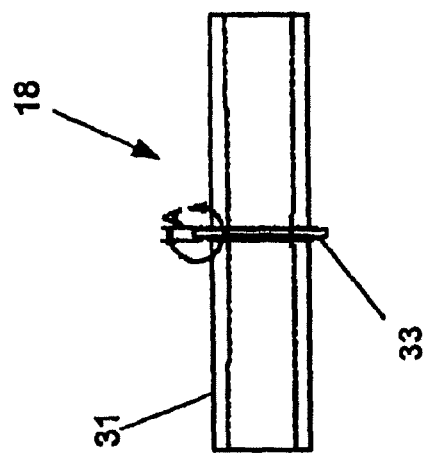
Figure 5A:
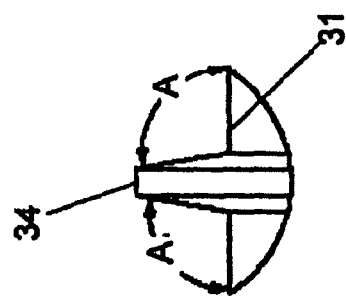
Figure 6:
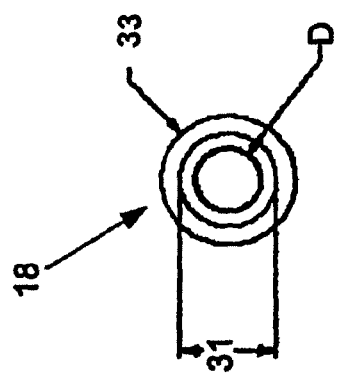
Figure 7:
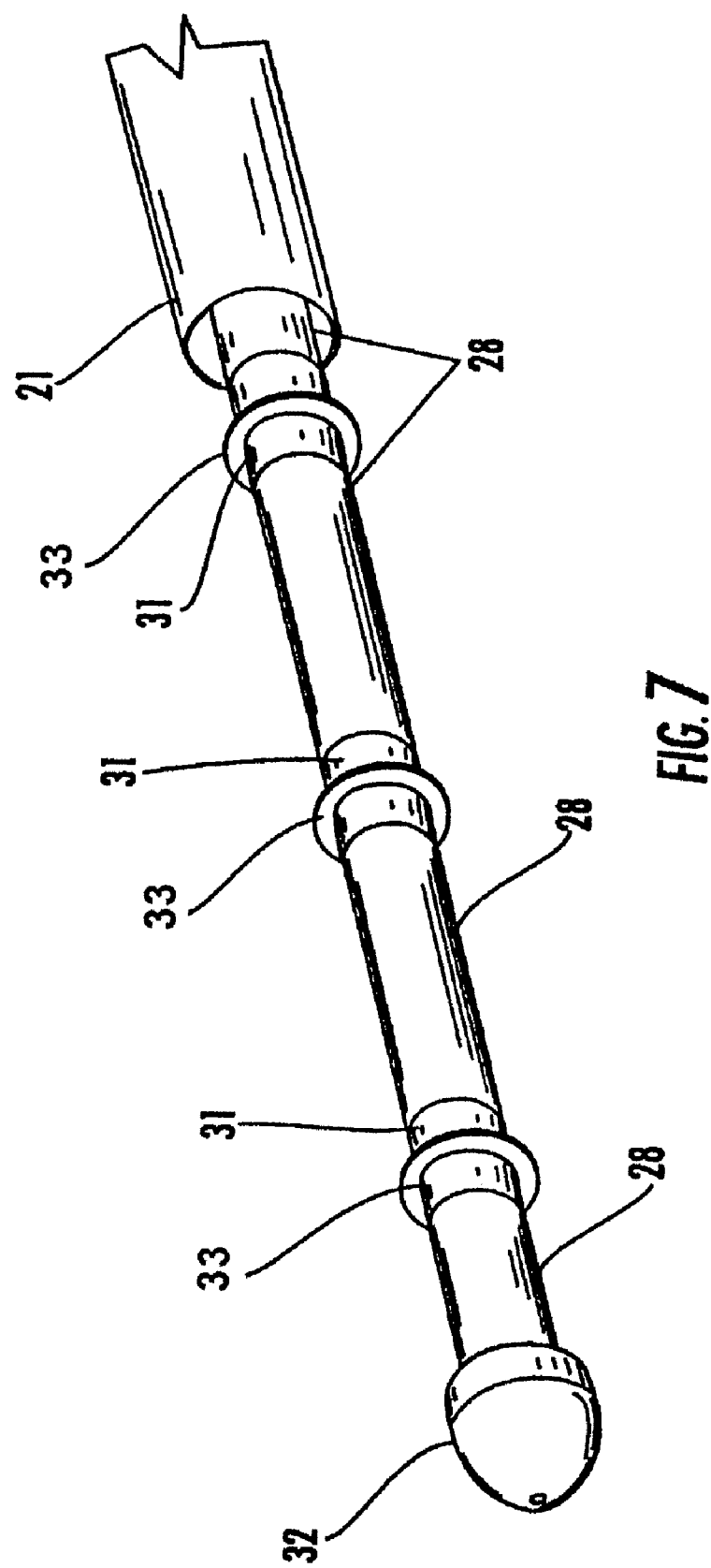
Figure 8:
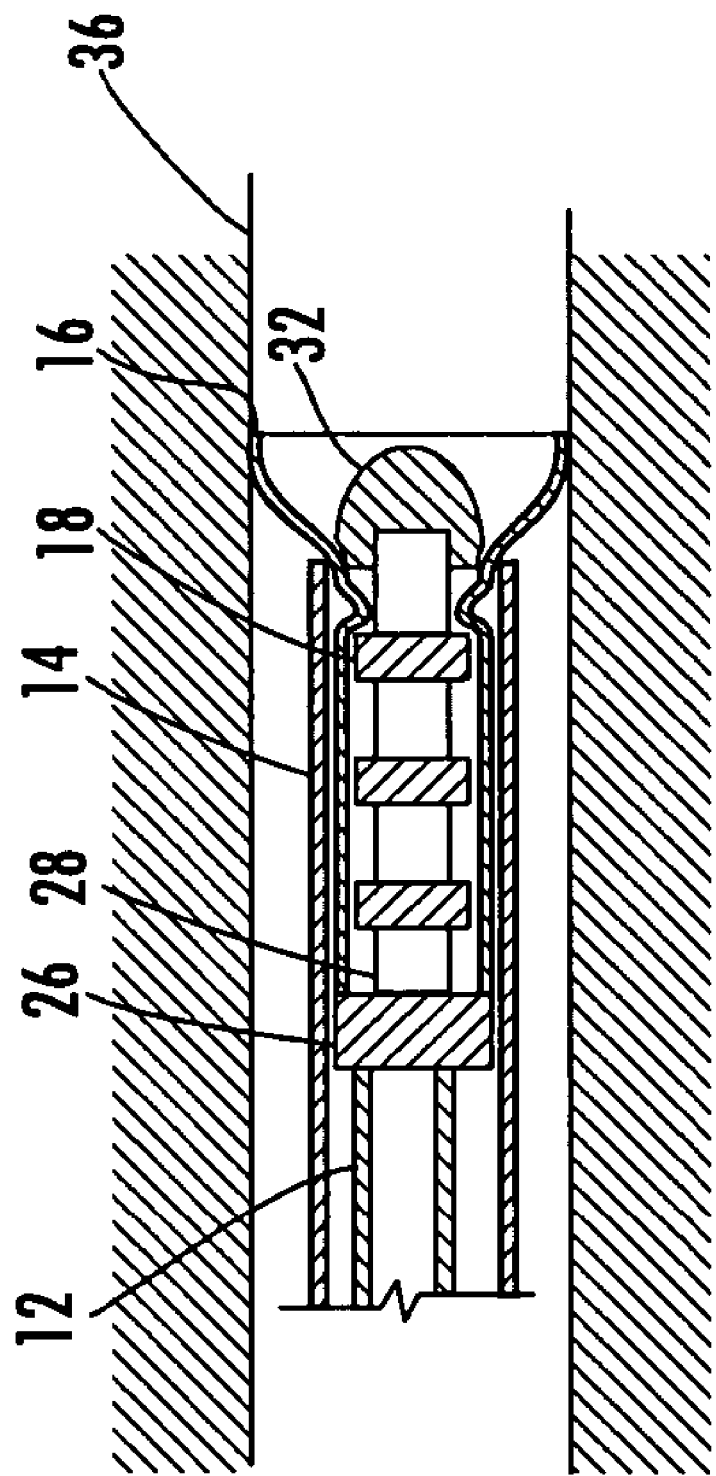

Having thus described the invention in general terms, reference will now be made to the accompanying drawings, which are not necessarily drawn to scale, and wherein:

FIG. 1 is a perspective view of a delivery device according to one embodiment of the present invention;

FIG. 2 is a side view of the delivery device shown in FIG. 1;

FIG. 2A is a cross-sectional view taken through line A-A of the delivery device shown in FIG. 2;

FIG. 3 is a side view of an outer tube assembly according to another embodiment of the present invention;

FIG. 3A is a cross-sectional view taken through line A-A of the outer tube assembly shown in FIG. 3;

FIG. 3B is an enlarged cross-sectional view of detail B of the outer tube assembly shown in FIG. 3A;

FIG. 4 is a side view of an inner tube assembly according to another embodiment of the present invention;

FIG. 4A is a cross-sectional view taken through line A-A of the inner tube assembly shown in FIG. 4;

FIG. 5 is a side view of an anchor according to another embodiment of the present invention;

FIG. 5A is an enlarged view of detail A of the anchor shown in FIG. 5;

FIG. 6 is an end view of the anchor shown in FIG. 5;

FIG. 7 is a partial perspective view of a delivery device according to another embodiment of the present invention; and FIG. 8 is a cross-sectional view of an anchor engaging an implantable device during deployment thereof according to an additional embodiment of the present invention.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

With reference to FIGS. 1-2A, a delivery device 10 is shown. The delivery device 10 generally includes an inner tube 12 positioned within an outer tube 14 and capable of sliding therein. The delivery device 10 also includes a deployment mechanism 20 that is capable of deploying an implantable device 16 out of the distal end of the outer tube 14 and adjacent to a target area. As will be explained in further detail below, one or more anchors 18 are positioned on the inner tube 12 to stabilize the implantable device 16 during deployment or repositioning of the device to reduce the incidence of foreshortening of the device.

Thus, the delivery device 10 is capable of being deployed within a lumen proximate to a target area. "Target area," as used herein, is not meant to be limiting, as the target area could be a stricture, lesion, tumor, occlusion, fistulae, or other complication where the lumen passageway has been significantly reduced or compromised. The delivery device 10 is typically utilized to deploy the implantable device 16 adjacent to a target area within a lumen.

It is understood that the delivery device 10 is applicable to a wide range of intraluminal applications. For example, the delivery device 10 could be used for implanting the implantable device 16 within lumina of the esophagus, trachea, arteries, or the biliary tract. The implantable device 16 could be, for example, a stent, drug delivery device, or other medical device or drug known to those skilled in the art now or in the future. Furthermore, any number of configurations of implantable devices 16 could be incorporated and still be within the present scope of the invention. An exemplary embodiment of the interstice geometry of a stent and methods of manufacturing the stent is disclosed in U.S. Patent Publication No. 20040127973, entitled "Removable Biliary Stent," which is assigned to the present assignee and is incorporated herein by reference.

Both the inner tube 12 and outer tube 14 are typically flexible for positioning and maneuvering the tubes within a lumen. Each of the inner 12 and outer 14 tubes are also typically transparent or semi-transparent, such that the inner tube is visible through the outer tube. Moreover, the inner tube 12 may include markers 15 for positioning and deploying the implantable device 16, although the inner and/or outer tubes could include markers if desired. For instance, the distal end of the outer tube 14 may include markers to locate the distal end of the implantable device 16. The inner tube 12 is slightly smaller in diameter than the outer tube 14 such that the inner tube may slide within the outer tube.

The outer tube 14 could have an incrementally larger diameter between its proximal and distal ends. In particular, FIGS. 3-3B illustrate that the distal portion of the outer tube 14 includes a transition region 19 that attaches to a sheath 21. The transition region 19 is defined integral with the outer tube 14 and extends outwardly at an angle to the larger diameter sheath 21. The sheath 21 is typically aligned adjacent to the implantable device 16 during positioning and deployment of the device at the target area. The sheath 21 may include one or more markers for locating the implantable device 16 within the lumen, and the sheath 21 is typically attached to the transition region 19 at one or more locations, such as with heat fusing or an adhesive.

However, each of the inner 12 and outer 14 tubes could also be various diameters and wall thicknesses along the length of each tube for varying flexibility and/or aiding in securing or deploying the implantable device 16. Thus, the transition region 19 and sheath 21 could be defined integrally with the outer tube 14 such that the outer tube is one unitary component. The diameter of the outer tube 12 could be uniform along its length and between its proximal and distal ends. Similarly, the inner 12 and outer 14 tubes may be various sizes and configurations to accommodate a desired implantable device 16. For example, the inner 12 and outer 14 tubes could be about 5 to 10 mm in diameter and about 500-800 mm in length. Moreover, although the term "inner tube" is used herein, it is understood that the inner tube could be a solid polymeric material or wire such that there is no aperture defined therethrough.

A substantial portion of the outer tube 14 includes an assembly of polymeric materials and a metal coil 24. For instance, the polymeric materials could be a polytetrafluoroethylene ("PTFE"), such as Teflon® ( (E.I. DuPont de Nemours and Co. Corp.), and a polyether block amide ("PEBA"), such as Pebax® (Atofina Corp.). Generally, when constructing the outer tube 14, a PTFE liner is placed over a mandrel, and the coil 24 is wound around the PTFE liner while positioned on the mandrel. The PEBA material is configured as a tube and slid over the wound coil 24 and the PTFE liner while the assembly is supported on the mandrel. The assembly is then heated such that the PEBA outer sheath and the PTFE liner are adhered together over the coil to form a tube assembly. The PTFE liner could be etched so that the PEBA material attaches or fuses to the PTFE material. FIG. 3B demonstrates that the coil 24 positioned within the outer tube 14 extends proximate to the transition region 19. The remaining portion of the outer tube 14 (i.e., the transition region 19) and sheath 21 are typically a combination of PTFE and PEBA materials. The interior of the outer tube 14 is thus a low-friction PTFE material, which allows the inner tube 12 to slide therethrough and requires lower deployment forces when retracting the sheath 21 during deployment of the implantable device 16. The coil 24 maintains a desired flexibility for the outer tube 14, but also prevents kinking or buckling when manipulating the outer tube within the lumen.

The inner tube 12 is also typically a polymeric material. For example, the inner tube could be a combination of PTFE and PEBA, as described above. Although the inner tube 12 illustrated in FIGS. 4 and 4A does not include a coil, a coil could be positioned within the inner tube in a similar manner as described with respect to the outer tube 14 if desired. A portion of the proximal end of the inner tube 12 extends within a metallic tube (e.g., stainless steel), where both the inner tube and metallic tube attach to a handle 30. The metallic tube aids in supporting and attaching the proximal end of the inner tube 12 to the handle 30. Thus, the proximal end of the inner tube 12 and metallic tube may be molded or otherwise attached to a portion of the handle 30, such as with an adhesive.

The deployment mechanism 20 typically includes one or more actuators 22 attached to the outer tube 14. The number of actuators 22 can be varied depending on the length of the implantable device 16. For example, there could be one actuator 22 for shorter implantable devices, or two or more actuators for longer implantable devices, as shown in FIGS. 1-3. When utilizing two or more actuators 22, the actuators may be operatively connected such that the actuators cooperate to deploy the implantable device 16. For example, FIGS. 3 and 3A illustrate that a pair of actuators 22 are connected to one another with a connector 38, where one actuator deploys the implantable device 16 partially, while the second actuator deploys the implantable device the remaining distance. The connector 38 is configured such that moving the proximal actuator 22 proximally also causes the distal actuator to move proximally. In particular, FIG. 2A shows that the connector 38 includes an aperture 35 defined therein, where the proximal actuator 22 abuts the connector and is capable of moving the connector and outer tube 14 proximally until the connector abuts the handle 30. In addition, the distal actuator 22 may slide proximally within the aperture 35 to retract the outer tube 14 and completely deploy the implantable device 16.

This arrangement of actuators 22 allows users of the delivery device 10 to deploy the implantable device 16 with one hand if desired. For example, with reference to FIGS. 1 and 2, a user would place a palm of the hand on the handle 30 of the delivery device 10 and extend his or her fingers of the same hand to pull proximally on the actuators 22 in succession. The outer tube 14 is coupled to the actuators 22 such that movement of the actuators causes concurrent sliding of the inner tube 12 within the outer tube 16. More specifically, the proximal end of the outer tube 14 is attached to an actuator 22 such that moving the actuator proximally causes the outer tube 14 to slide proximally over the inner tube 12, while the inner tube remains stationary.

It is understood that various techniques could be employed to deploy the implantable device 16. As such, the deployment mechanism 20 could be various devices or actuators capable of deploying the implantable device 16 distally out of the outer tube 14. For example, the actuators 22 could be configured to slide the inner tube 12 distally within the outer tube 14 such that the outer tube remains stationary. Moreover, the mechanism 20 could be various sizes and configurations. For instance, although the actuators 22 are T-shaped, the actuators could be configured as a trigger to grip the actuator.

A pusher 26 is positioned on the inner tube 12 such that the pusher aligns with a proximal end of the implantable device 16 when deploying the implantable device. As shown in FIGS. 4 and 4A, the pusher 26 is positioned over the inner tube 12 and is slightly larger in diameter than the inner tube. The proximal end of the implantable device 16 is typically positioned adjacent to the pusher 26, and the pusher could be colored or include a marker for identifying the proximal end of the implantable device within the lumen.

It is understood that the pusher 26 shown and described above may include various sizes and configurations in alternative embodiments of the present invention. For instance, the pusher 26 could be integrally formed with the inner tube 12 such that pusher is not a separate component of the inner tube. It is noted that although the term "pusher" is used herein, the pusher 26 does not typically push the implantable device 16. In contrast, the inner tube 12 and pusher 26 remain stationary while the outer tube 14 is retracted. However, the pusher 26 may be configured to advance the implantable device 16 such that the inner tube 12 may be moved distally while the outer tube 14 remains stationary or is moved concurrently in a proximal direction.

FIGS. 4 and 4A demonstrate the delivery device 10 includes anchors 18 that extend outwardly from the inner tube 12 at spaced intervals about the circumference of the inner tube. The implantable device 16 is positioned between the anchors 18 and the sheath 21 during deployment of the device. The anchors 18 are generally spaced along the inner tube 12 such that the anchors distribute the force applied along the implantable device 16. The anchors 18 are capable of frictionally engaging the implantable device 16 and/or the sheath 21, or could be configured to engage openings defined in the implantable device. Additionally, the anchors 18 are also capable of engaging the implantable device 16 to reposition the delivery device 10 or the implantable device when the implantable device is partially deployed. For example, after partially deploying the implantable device 16, the delivery device 10 could be moved proximally to reposition the implantable device within the lumen.

According to an additional aspect of the present invention, the anchors 18 are configured as engagement members that are spaced away from the implantable device 16 prior to deployment but are configured to engage the implantable device during deployment thereof. More specifically, the implantable device 16 is positioned within the delivery device 10 (i.e., prior to deployment) such that the engagement members do not initially engage the implantable device. As shown as in FIG. 8, during deployment, friction between the outer tube 14 and the implantable device 16 may cause a portion of the implantable device to become distorted (e.g., a portion of the implantable device may protrude inwardly) as the outer tube is retracted relative to the inner tube 12. As such, the engagement members may contact the distorted portion(s) of the implantable device 16 to thereby overcome the friction between the implantable device and the outer tube 14. Thus, the engagement members aid in overcoming friction between the implantable device 16 and the outer tube 14, as well as preventing foreshortening of the implantable device within the lumen 36.

The anchors 18 are positioned over the inner tube 12 such that the anchors are freely rotatable about the inner tube. Each of the anchors 18 are separated by a spacer 28, where the spacer is also positioned over the inner tube 12 and is freely rotatable thereabout. A tip 32 is attached to the end of the inner tube 12 to axially restrain the anchors 18 and spacers 28 on the inner tube and adjacent to the pusher 26, while still allowing the anchors and spacers to rotate about the inner tube.

As depicted in FIGS. 5-7, each anchor 18 includes an annular member 33 extending outwardly and radially from a cylindrical member 31. FIG. 5A demonstrates that the annular member 33 includes angles A that define a chamfer about the circumference of the annular member. Moreover, the cylindrical member 31 includes an aperture extending therethrough and has a diameter D that is larger than the inner tube 12 to facilitate rotation of the anchor 18 about the inner tube.

At least a portion of the inner tube 12 extends between the handle 30 and the tip 32. As also shown in FIGS. 4 and 4A, the diameter of the inner tube 12 between the handle 30 and pusher 26, as well as the diameter of the spacers 18 and cylindrical member 31 are substantially the same. Accordingly, the diameter of the inner tube 12 distal of the pusher 26 is typically reduced in diameter. For instance, if the portion of the inner tube 12 located between the handle 30 and the proximal end of the pusher 26 is a combination of PTFE and PEBA, the portion of the inner tube distal of the pusher could be PTFE or PEBA to reduce the diameter. However, if desired, it is understood that the diameter of the inner tube 12 could be constant between its proximal and distal ends.

Although the illustrated embodiments are preferred, there could be various numbers, sizes, and configurations of anchors 18 and spacers 28 in additional aspects of the present invention. For example, the collective distance between the distal end of the pusher 26 and the tip 32 could be about 70-150 mm, the spacer 28 could be about 5-40 mm in length, the diameter D could be about 2-5 mm, the angle A could be about 90-150 degrees, the diameter of each annular member 33 could be about 5-7 mm, and the length of the cylindrical member 31 could be about 15-25 mm Moreover, although FIGS. 4 and 7 show three anchors 18, there could be as few as one or more than one (e.g., two, four, etc.) anchor 18 extending over the inner tube 12 to prevent the implantable device 16 from compressing along its length during deployment of the device. Furthermore, the anchors 18 could be various configurations, such that that the annular member 33 could be a protuberance, bump, or raised surface extending outwardly from the cylindrical member 31 that is capable of contacting a portion of the inner surface of the implantable device 16 to apply a force on the implantable device 16 and outer sheath 21 (before and/or during deployment of the implantable device), or that is capable of extending through one or more openings defined in the implantable device to engage the implantable device. As such, the annular member 33 need not extend completely about the circumference of the cylindrical member 31 and may be non-annular. Therefore, it is understood that the number, size, and configuration of the anchors 18 and spacers 28 are modifiable to accommodate a particular implantable device 16 or to apply a desired amount of force to the implantable device and the sheath 21.

The anchors 18 and spacers 28 are typically polymeric materials, such as low density polyethylene ("LDPE"). The anchors 18 and spacers 28 could be formed using various techniques, such as injection molding. Typically, the annular member 33 and cylindrical member 31 are integrally formed but there may be instances where the annular member is separately attached to the cylindrical member. Moreover, there could be instances where the spacers 28 are formed integrally with the anchors 18, or the spacers are omitted, such as when several anchors are employed or where the cylindrical members 30 are abutted against one another.

To assemble the delivery device 10, the inner 12 and outer 14 tubes are formed, as described above, and the outer tube is positioned over the inner tube. The sheath 21 is also attached to the distal end of the outer tube. The pusher 26, anchors 18, and spacers 28 are slid on the inner tube such that the anchors and spacers are capable of rotating about the inner tube. The tip 32 is then attached to the distal end of the inner tube 12 to secure the pusher 26, anchors 18, and spacers 28 on the inner tube and adjacent to one another. Because the pusher 26, anchors 18, and spacers 28 are not fixedly attached to the inner tube 12, each could be replaced and reassembled to accommodate various implantable devices 16.

The implantable device 16 is deployed within a lumen and proximate to a target area using techniques known to those skilled in the art. For instance, the implantable device may be introduced orally with the delivery device 10, through the lumen, and proximate to a target area. The implantable device 16 is typically contracted to a smaller first diameter from a relaxed position. Once contracted, the implantable device 16 is positioned within the outer tube 14 of the delivery device proximate to the distal end of the outer tube. The inner tube 12 is positioned within the outer tube 14 such that the distal end of the inner tube is positioned proximate to the proximal end of the implantable device 16.

The implantable device 16 is positioned proximate to the target area such that when the implantable device is deployed from the sheath 21, the implantable device, if formed from an expansible material, can expand to receive the target area and even expand the diameter of the target area. In particular, the distal end of the sheath 21 is positioned proximate to a distal end of the target area. The outer tube 14 and sheath 21 are then retracted over the inner tube 12 using one or more actuators 22, while the pusher 26 supports the proximal end of the implantable device 16. The implantable device 16 is typically deployed incrementally along its length so that a more controlled deployment and accurate position is achieved.

The present invention includes several advantages. The anchors 18 provide a compressive force to the implantable device 16 and the sheath 21 to stabilize the implantable device during deployment of the device. As a result, the incidence of foreshortening is reduced, which results in more accurate alignment of the implantable device 16 with a target area. Because the implantable device 16 is more accurately positioned within the lumen, the probability of misalignment and subsequent procedures to correct the alignment is reduced. The anchors 18 are also positioned over the inner tube 12, which allows for easier manufacturing and assembly of the delivery device 10. Because the pusher 26, anchors 18, and spacers 28 are not fixedly attached to the inner tube 12, each could be replaced and reassembled to accommodate various implantable devices 16. Moreover, the delivery device 10, including the anchors 18, is applicable to a wide range of applications, such as deploying implantable devices in a variety of lumina.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A delivery device for positioning and deploying an implantable device within a lumen comprising:
    a longitudinal outer tube having proximal and distal ends, wherein the implantable device is capable of being positioned proximate to the distal end of the outer tube;
    a longitudinal inner tube slidably disposed within the outer tube and having proximal and distal ends, wherein the inner tube is configured to underlie at least a portion of the implantable device;
    a mechanism coupled to at least one of the inner and outer tubes and operable to deploy the implantable device within the lumen;
    at least one anchor positioned on the inner tube and being freely rotatable with respect thereto, wherein each anchor is capable of engaging at least a portion of the implantable device for stabilizing the implantable device during deployment thereof; and
    at least one spacer positioned on the inner tube and being freely rotatable with respect thereto, wherein the spacer is independently and freely rotatable with respect to the at least one anchor.

2. The delivery device according to claim 1, wherein the outer tube comprises a coil positioned therein.

3. The delivery device according to claim 2, wherein the coil of the outer tube extends proximally of its distal end.

4. The delivery device according to claim 1, wherein the outer tube comprises a sheath attached to the distal end of the outer tube.

5. The delivery device according to claim 4, wherein the sheath is larger in diameter than the outer tube, and wherein the implantable device is capable of being positioned within the sheath prior to deployment of the implantable device.

6. The delivery device according to claim 1, wherein each of the inner and outer tubes comprises a semi-transparent polymeric material.

7. The delivery device according to claim 6, wherein the polymeric material comprises at least one of polytetrafluoroethylene and polyether block amide.

8. The delivery device according to claim 1, wherein the mechanism comprises at least one actuator coupled to the outer tube.

9. The delivery device according to claim 1, further comprising a plurality of anchors positioned on the inner tube that are independently and freely rotatable with respect to one another and the at least one spacer.

10. The delivery device according to claim 1, wherein each anchor comprises an annular member that extends outwardly and radially about at least a portion of the circumference of the inner tube, wherein each annular member is configured to engage an interior of the implantable device during deployment thereof.

11. The delivery device according to claim 10, wherein each annular member extends outwardly and radially from a cylindrical member.

12. The delivery device according to claim 1, wherein each anchor is capable of applying a compressive force on at least a portion of the interior of the implantable device to frictionally engage the implantable device during deployment thereof.

13. The delivery device according to claim 1, wherein the at least one spacer is positioned adjacent to a respective anchor.

14. A delivery device for positioning and deploying an implantable device within a lumen comprising:
    a longitudinal outer tube having proximal and distal ends, wherein the implantable device is capable of being positioned proximate to the distal end of the outer tube;
    a longitudinal inner tube slidably disposed within the outer tube and having proximal and distal ends, wherein the inner tube is configured to underlie at least a portion of the implantable device;
    a mechanism coupled to at least one of the inner and outer tubes and operable to deploy the implantable device within the lumen;
    a plurality of anchors independent of one another and positioned on the inner tube, wherein each anchor is capable of engaging at least a portion of the implantable device for stabilizing the implantable device during deployment thereof; and
    at least one spacer independent of the plurality of anchors and positioned on the inner tube and adjacent to at least one anchor, wherein each anchor and each spacer are positioned on the inner tube such that each anchor and each spacer are freely and independently rotatable about the inner tube with respect to one another.

15. The delivery device according to claim 14, wherein each spacer is positioned between a pair of anchors.

16. The delivery device according to claim 14, wherein the inner tube comprises a pusher positioned proximally of the distal end of the inner tube, and wherein a proximal end of the implantable device is capable of being
    positioned adjacent to the pusher during deployment of the implantable device.

17. The delivery device according to claim 16, wherein a diameter of the inner tube proximally of the pusher is larger than a diameter of the inner tube distally of the pusher.

18. The delivery device according to claim 14, wherein each anchor comprises an annular member that extends outwardly and radially about at least a portion of the circumference of the inner tube, wherein each annular member is configured to engage an interior of the implantable device during deployment thereof.

19. The delivery device according to claim 18, wherein each annular member extends outwardly and radially from a cylindrical member.

20. The delivery device according to claim 19, wherein a diameter of each spacer is substantially the same as a diameter of each cylindrical member.

21. The delivery device according to claim 14, wherein each anchor is capable of applying a compressive force on the interior of the implantable device and the outer tube to frictionally engage the implantable device.

22. A method for manufacturing a delivery device for positioning and deploying an implantable device within a lumen, the method comprising:

forming a longitudinal inner tube having proximal and distal ends;

positioning at least one anchor and a plurality of spacers on the inner tube such that each anchor and each spacer are independently and freely rotatable with respect to one another;

forming an outer tube having proximal and distal ends; and positioning the outer tube over the inner tube such that the outer tube is capable of sliding over the inner tube.

23. The method according to claim 22, further comprising attaching a sheath to the distal end of the outer tube, wherein the sheath is capable of accommodating an implantable device therein.

24. The method according to claim 22, further comprising positioning a pusher on the inner tube and adjacent to at least one anchor, and wherein positioning comprises positioning the at least one anchor distally of the pusher.

25. The method according to claim 24, wherein forming comprises forming the inner tube such that a diameter of the inner tube proximally of the pusher is larger than a diameter of the inner tube distally of the pusher.

26. The method according to claim 25, further comprising attaching a tip to the distal end of the inner tube to restrain the at least one anchor and the at least one spacer on the inner tube between the pusher and the tip.

27. The method according to claim 22, further comprising forming the at least one anchor with injection molding prior to positioning the anchor on the inner tube.

28. The method according to claim 22, further comprising coupling a deployment mechanism to at least one of the inner and outer tubes, wherein the deployment mechanism is capable of deploying the implantable device within the lumen.

29. A delivery device for positioning and deploying an implantable device within a lumen comprising:

an elongate first member having a longitudinal direction;

a second member slidable with respect to the first member and defining a space therebetween configured to hold the implantable device;

wherein sliding of the first and second members relative to each other opens the space and deploys the implantable device from the space and into the lumen; and a plurality of engagement members independent of one another and linearly spaced apart from one another in the longitudinal direction of the first member, the engagement members disposed on one of the first and second members, wherein the engagement members are spaced from an interior of the implantable device prior to relative sliding of the first and second members and become engaged with a portion of the interior of the implantable device as the first and second members slide relative to each other so as to overcome friction between the implantable device and the one of the first and second members not supporting the engagement members.

30. The delivery device according to claim 29, wherein each engagement member is positioned on one of the first and second members such that each engagement member is independently and freely rotatable thereabout with respect to one another.

31. The delivery device according to claim 29, wherein each engagement member comprises an annular member that extends outwardly and radially about at least a portion of the circumference of one of the first and second members, wherein each annular member is configured to engage an interior of the implantable device during deployment thereof.

32. The delivery device according to claim 31, wherein each engagement member extends outwardly and radially from a cylindrical member.

33. The delivery device according to claim 29, further comprises at least one spacer independent of the plurality of the engagement members and positioned on one of the first and second members and adjacent to a respective engagement member.

34. The delivery device according to claim 29, wherein the first member comprises an outer tube and the second member comprises and inner tube, and wherein the inner tube is positioned within the outer tube.

35. The delivery device according to claim 34, wherein the plurality of engagement members are supported by the inner tube and are disposed coaxially to one another.

36. The delivery device according to claim 29, further comprising a mechanism coupled to at least one of the first and second members and operable to slide the first and second members relative to each other to deploy the implantable device within the lumen.

* * * * *